(12) United States Patent
VanPelt

(10) Patent No.: US 11,696,996 B2
(45) Date of Patent: Jul. 11, 2023

(54) CAPNOGRAPHY TUBE FITTING

(71) Applicant: Accutron, Inc., Phoenix, AZ (US)

(72) Inventor: Benjamin F. VanPelt, Phoenix, AZ (US)

(73) Assignee: Hu-Friedy Mfg. Co., LLC, Chicago, IL (US)

( * ) Notice: Subject to any disclaimer, the term of this patent is extended or adjusted under 35 U.S.C. 154(b) by 987 days.

(21) Appl. No.: 16/446,743

(22) Filed: Jun. 20, 2019

(65) Prior Publication Data

US 2020/0001035 A1 Jan. 2, 2020

Related U.S. Application Data

(60) Provisional application No. 62/690,644, filed on Jun. 27, 2018.

(51) Int. Cl.
| | | |
|---|---|---|
| *A61M 16/08* | (2006.01) | |
| *A61M 16/06* | (2006.01) | |
| *A61B 5/08* | (2006.01) | |
| *A61B 5/083* | (2006.01) | |
| *A61B 5/097* | (2006.01) | |

(52) U.S. Cl.
CPC ......... *A61M 16/085* (2014.02); *A61B 5/0836* (2013.01); *A61B 5/097* (2013.01); *A61M 16/06* (2013.01); *A61M 2210/0618* (2013.01)

(58) Field of Classification Search
CPC .......... A61M 15/0065; A61M 15/0086; A61M 15/009; A61M 16/0009; A61M 16/0012; A61M 16/04; A61M 16/0404; A61M 16/042; A61M 16/0434; A61M 16/0445; A61M 16/0459; A61M 16/0465; A61M 16/0486; A61M 16/06; A61M 16/0672; A61M 16/08; A61M 16/0816; A61M 16/0833; A61M 16/085; A61M 16/10; A61M 16/208; A61M 2016/0021; A61M 2016/103; A61M 2205/8225; A61M 2209/06; A61M 2230/432
See application file for complete search history.

(56) References Cited

U.S. PATENT DOCUMENTS

| | | | | |
|---|---|---|---|---|
| 4,602,644 A * | 7/1986 | DiBenedetto | .......... | A61B 7/003 128/207.18 |
| 4,838,258 A * | 6/1989 | Dryden | ............. | A61M 16/0833 128/204.18 |
| 6,014,972 A * | 1/2000 | Sladek | .................. | A61M 16/08 128/203.15 |
| 6,273,087 B1 * | 8/2001 | Boussignac | ........... | A61M 16/12 128/204.22 |

(Continued)

*Primary Examiner* — Annette Dixon

(57) ABSTRACT

Provided herein is a capnography fitting for use in a capnography system wherein the capnography fitting is configured to fit inhalation masks of various sizes and shapes so that viable carbon dioxide readings can be obtained from an air sample obtained from a patient's exhaled gas. The fitting includes a rigid tube having a proximal end inlet configured to receive an inhalation gas and to slidably engage a mixed gas fitting, and a distal end outlet configured to slidably engage directly to an inlet of an inhalation mask configured to cover a nose and/or mouth. The tube also includes an angled port in fluid communication with and disposed adjacent to the proximal end inlet or the distal end outlet. Methods and kits are also provided.

11 Claims, 14 Drawing Sheets

(56) References Cited

U.S. PATENT DOCUMENTS

| | | | |
|---|---|---|---|
| 8,312,882 B2* | 11/2012 | Boussignac | A61M 16/127 128/206.26 |
| 9,199,053 B1* | 12/2015 | Allum | A61M 16/085 |
| 2005/0005936 A1* | 1/2005 | Wondka | A61M 16/042 128/204.23 |
| 2005/0257791 A1* | 11/2005 | Biederman | A61M 16/06 128/204.23 |

* cited by examiner

CAPNOGRAPHY TUBE FITTING

PRIORITY

This application claims priority to and the benefit of U.S. Provisional application with Ser. No. 62/690,644, filed on Jun. 27, 2018, entitled CAPNOGRAPHY TUBE FITTING, which is herein incorporated by reference in its entirety.

BACKGROUND

Inhalation systems or respiratory systems are commonly used during medical and dental procedures for administering gases to a patient such as anesthetics, analgesics, oxygen and nitrous oxide. During administration of these gases, it is beneficial for a medical or dental practitioner to monitor the carbon dioxide concentration in the exhaled breath of the patient via capnography. Measurements of the carbon dioxide concentration in a patient's breath can be taken by a capnography device and the results are displayed in a graphical format in the shape of a waveform called a capnogram. Typically, capnograms depict carbon dioxide concentration over time.

Capnography devices have been used in various healthcare fields for some time. The amount of carbon dioxide exhaled from a patient's breath is a useful measurement to determine how well a patient is breathing especially when an anesthetic, analgesic or other medication is used to sedate the patient. For example, if the patient has reduced breathing during sedation, carbon dioxide will not be able to be exhaled by the patient. This lack of exhalation of carbon dioxide will make the capnogram show a low carbon dioxide reading, which will trigger an alarm that alerts medical staff to the problem. In this way, a compromised respiratory system can be detected early in the medical or dental procedure.

Often, inhalation systems or respiratory systems include a source of the inhalation gas and an apparatus to deliver the gas to the respiratory system of the patient. A breathing device, such as a disposable inhalation mask, is fitted on the face of the patient to cover the nose and/or the mouth. The inhalation gas source, which may be either portable or fixed, usually includes a flow regulator. A delivery conduit, generally in the form of a flexible hose, communicates between the inhalation gas source and the breathing device.

The inhalation system may include a capnography scavenging apparatus having a sampling tube and a return conduit extending from the breathing device to a vacuum source.

When the inhalation system is used and the patient is breathing, the sampling tube contains a sample of the air from the patient's breathing during the medical or dental procedure. The capnography scavenging apparatus is coupled to the capnography device, which produces a graphical read out of the carbon dioxide contained in the patient's exhaled gas.

Generally, the capnography scavenging apparatus is fixed to the inhalation mask and changing the location of the sampling tube cannot be done simply. By fixing the capnography scavenging apparatus including the sampling tube to one location, it can prevent the apparatus from obtaining an optimal reading from the patient. Further, the fixed apparatus cannot be adapted from a right-handed user to a left-handed user or from a left-handed user to a right-handed user easily. This can make using the capnography scavenging apparatus limited and not versatile for multiple users.

Currently, in order to change the location of the sampling tube of the capnography scavenging apparatus, a user, such as a clinician, has to manually punch hole(s) into the wall(s) of the mask in order to make changes to the mask's dynamics. This can be a crude task and difficult to perform either before or during the medical or dental procedure. Additionally, movement of the sampling tube becomes cumbersome. Further, changing the location of the sampling tube in this manner is not time efficient and the hole created by the user may cause the mask to no longer have an air tight seal, which may further disrupt gas flow and may lead to less accurate capnography readings as gas escapes from the seal.

Therefore, there is a need for a capnography fitting that is suitable for use with both right handed and left-handed users. There is also a need for an improved capnography fitting that allows the sampling tube to be easily inserted into and removed from the desired location in the inhalation mask. A capnography fitting that fits inhalation masks of various sizes and shapes would be beneficial.

SUMMARY

A capnography fitting is provided that is compatible with an inhalation mask and can easily be inserted by both right handed and left-handed users. The capnography fitting provided fits inhalation masks of various sizes and shapes. In some embodiments, the capnography fitting provided allows the sampling tube to be easily inserted into and removed from the desired location in the inhalation mask.

In some embodiments, there is a capnography fitting comprising a tube having a proximal end inlet and a distal end outlet. The tube has an angled port in fluid communication with and disposed adjacent to the proximal end inlet or the distal end outlet.

In some embodiments, there is a capnography fitting comprising a tube having a proximal end inlet and a distal end outlet. The tube has an angled port in fluid communication with and disposed adjacent to the proximal end inlet and the distal end outlet, the distal end outlet configured to engage an inlet of a nasal mask.

In some embodiments, a kit for capnography monitoring is provided. The kit comprises a capnography fitting comprising a tube having a proximal end inlet and a distal end outlet, the tube having an angled port in fluid communication with and disposed adjacent to the proximal end inlet and the distal end outlet; and instructions for assembling the kit for capnography monitoring.

In some embodiments, a method of assembling a capnography system is provided. The method comprises: providing a capnography fitting, the capnography fitting comprising a tube having a proximal end inlet and a distal end outlet, the tube having an angled port in fluid communication with and disposed adjacent to the proximal end inlet and the distal end outlet; inserting a first end of a mixed gas fitting into the proximal end inlet of the tube; coupling a second end of the mixed gas delivery fitting to a delivery hose that is attached to a vacuum source; coupling the distal end outlet of the tube to an inlet of a nasal mask; and coupling a connector to an outlet of the nasal mask that is engaged with a vacuum hose, the vacuum hose being connected to a vacuum source to assemble the capnography system.

In some embodiments, a method of monitoring a patient's respiratory functions is provided. The method comprising: attaching a nasal mask to a nose of the patient, the nasal mask having an inlet to receive inhalation gas and an outlet to discharge exhalation gas, the nasal mask comprising a capnography fitting comprising a tube having a proximal end inlet and a distal end outlet, the tube having an angled port in fluid communication with and disposed adjacent to the proximal end inlet and the distal end outlet, the distal end outlet of the tube slidably engaging the inlet of the nasal mask; providing inhalation gas to the patient through the inlet of the nasal mask; and obtaining a sample of the exhalation gas from the angled port to monitor the patient's respiratory functions.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings where:

Figure 1:
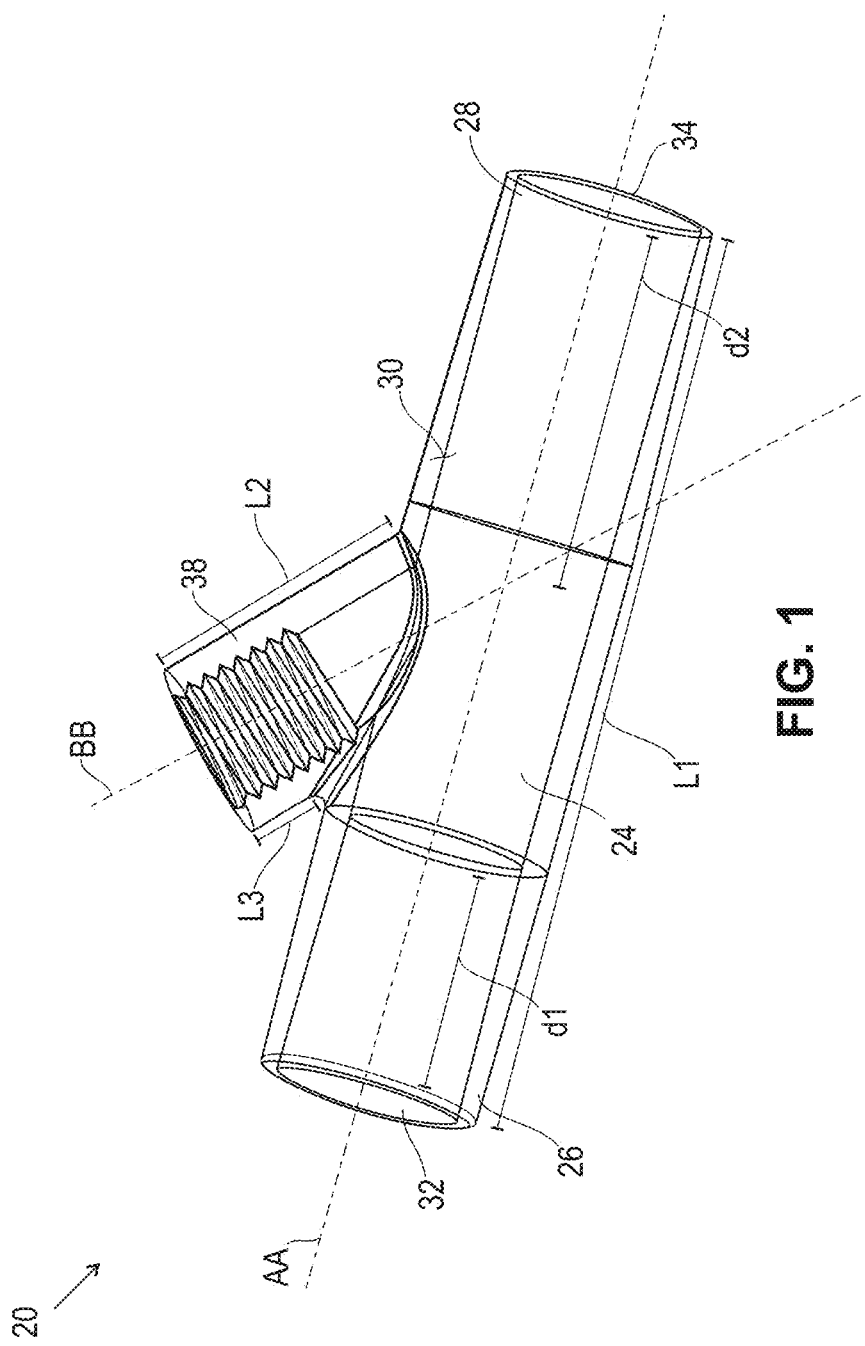
FIG. 1 illustrates a perspective view of an embodiment of a capnography fitting having an angled port for use with an inhalation mask, such as for example, a nasal mask.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

It is noted that, as used in this specification and the appended claims, the singular forms "a," "an" and "the" include plural referents unless expressly and unequivocally limited to one referent. Thus, for example, reference to "a connector" includes one, two, three or more connectors.

We refer now to the drawings wherein depicted elements are not necessarily shown to scale and wherein like or similar elements are designated by the same reference numeral through the several views.

Referring to the drawings in general, it will be understood that the illustrations are for the purpose of describing particular embodiments of the disclosure and are not intended to be limiting thereto.

While most of the terms used herein will be recognizable to those of ordinary skill in the art, it should be understood that when not explicitly defined, terms should be interpreted as adopting a meaning presently accepted by those of ordinary skill in the art.

A capnography fitting is provided that is compatible with an inhalation mask (e.g., nasal mask) and can easily be inserted by both right handed and left-handed users. The capnography fitting provided fits inhalation masks of various sizes and shapes. In some embodiments, the capnography fitting provided allows the sampling tube to be easily inserted to and removed from the desired location in the inhalation mask.

In some embodiments, the present application provides, among other things, a capnography fitting that is designed to connect to an inhalation mask (e.g., nasal mask) so that viable carbon dioxide readings can be obtained from an air sample obtained from a patient's exhaled gas. The samples are then analyzed and displayed on the capnography device in order to track the patient's breathing patterns as a method to monitor the patient's breathing and respiratory status in real time.

Analyzing the capnogram generated from the capnography device may yield valuable information about the patient's clinical status. A normal capnogram exhibits one or more typical waveforms, each one represents a single respiratory cycle, and deviations from the normal waveform may indicate the clinical situation of the patient. For example, if the patient has reduced breathing during sedation, carbon dioxide will not be able to be exhaled by the patient. This lack of exhalation of carbon dioxide will make the capnogram show a low carbon dioxide reading, which will trigger an alarm (e.g., an audio and or visible alarm) that alerts medical staff to the problem.

In some embodiments, a capnography fitting is provided that is disposable for a single use. The fitting may be made of sterilizable materials and packaged with one or more disposable sample tubes such that a user can conveniently insert a sample tube into the capnography fitting or install the capnography fitting into a circuit of a capnography system, which can allow easy change and disposal of the sample tube once used.

In some embodiments, the fitting can be used with a nasal mask available from Accutron, Inc. of Phoenix, Ariz. in scented and unscented flavors and adult, large adult and pediatric sizes under the name Axess™. Suitable nasal masks for use with the capnography fitting are described in U.S. Patent Publication No. 2017/0361057 assigned to Accutron, Inc. of Phoenix, Ariz.

In some embodiments, the capnography fitting provides easy and reliable access to both sides of a nasal mask. The capnography fitting provided in the present application can be easily slidably installed into the nasal mask and does not require extensive manual modification by the user (e.g., placing holes in the nasal mask and/or tubing to obtain sampled air).

In some embodiments, the capnography fitting is reusable, and the capnography fitting can remain in a circuit of a capnography system for normal sterilization. In some embodiments, in the reusable configuration, the capnography fitting can be sterilized and reused while the sampling tube can be removed from the capnography fitting and disposed of when the procedure is completed.

Capnography Fitting

A disposable capnography fitting 20 is provided, as shown in FIGS. 1-3 and 6 that can be used with components of a capnography system 22, as shown in FIGS. 12-15. The fitting is suitable for universal use for both left handed and right-handed users and is configured for use with a variety of inhalation masks, such as for example nasal masks as described herein. The fitting provides an air-tight seal for gases entering and exiting the inhalation mask (e.g., nasal mask).

The fitting includes a tube 24, which is a single tube, having a proximal end 26, a distal end 28 and a longitudinal axis AA disposed therebetween, as shown in FIG. 1. The tube of the fitting is configured to receive an inhalation gas, such as, for example, oxygen, carbon dioxide, nitrogen, an anesthetic gas, such as nitrous oxide, halogenated agents, such as, for example, halothane (Fluothane®), enflurane (Ethrane®), isoflurane (Forane®), desflurane (Suprane®), and sevoflurane (Ultane®) or a combination thereof.

The tube has a length L1, as shown in FIG. 1. Length L1 can be from about 20 to about 70 mm. The length L1 can be about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 mm.

Figure 2:
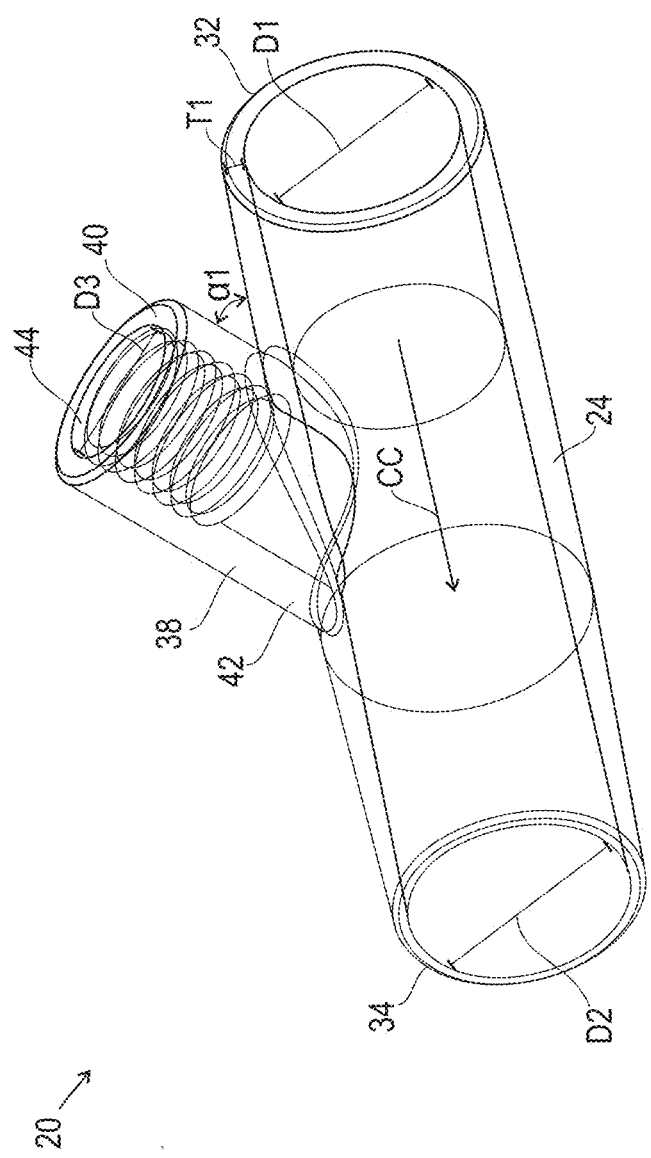
FIG. 2 illustrates a perspective view of the capnography fitting of FIG. 1.

An exterior surface 30 of the tube defines a first opening, such as a proximal end inlet 32 at the proximal end of the tube. The proximal end inlet is configured to receive the inhalation gas, and to couple to (e.g., slidably engage) a mixed gas fitting, as described herein. The proximal end inlet includes a diameter D1, as shown in FIG. 2. Diameter D1 can have a diameter of from about 5 to about 15 mm. Diameter D1 can have a diameter of about 5, 6, 7, 8, 9, 10, 11, 12, 13, 14 or 15 mm.

The exterior surface of the tube defines a second opening, such as a distal end outlet 34 at the distal end of the tube. The distal end outlet is configured to couple with (e.g., slidably engage) an inlet of an inhalation mask, as described herein. The distal end outlet includes a diameter D2, as shown in FIG. 2. Diameter D2 can have a diameter of from about 5 to about 15 mm. Diameter D2 can have a diameter of about 5, 6, 7, 8, 9, 10, 11, 12, 13, 14 or 15 mm. In some embodiments, the diameter D1 of the proximal end inlet is equal to the diameter D2 of the distal end outlet. The diameter D1 of the proximal end inlet can, in some embodiments, be greater than or less than the diameter D2 of the distal end outlet. In the embodiment shown, the diameters D1 and D2 are the same and constant throughout the first tube.

An inner surface 36 extends between the proximal end and the distal end of the tube which defines a hollow interior. The tube can have the same or a varying thickness T1 throughout. For example, the thickness of the tube can be the same or different at the proximal end and the distal end. The thickness T1 can be from about 0.1 mm to about 3 mm. The thickness can be about 0.1, 0.2, 0.3, 0.4, 0.5, 0.6, 0.7, 0.8, 0.9, 1, 2 or 3 mm.

The distal end outlet of the tube is configured to slidably engage the inlet of the nasal mask and can be easily inserted into the inlet of a nasal mask and can provide a snug fit with the inlet. The capnography fitting can be removed from the mask once the procedure is over and, in some embodiments, discarded after use. In some embodiments, the tube can be tapered at the proximal end and distal end. Alternatively, the proximal end or the distal end may be tapered.

The fitting includes an angled port 38. The angled port can be monolithic with the tube and is configured to receive a sampling tube, as described herein. The angled port is in fluid communication with and disposed adjacent to the proximal end inlet or to the distal end outlet or both the proximal end inlet and the distal end outlet. Shown in FIG. 1, the proximal opening is a closer distance to the proximal end of the angled port as compared to the distal end outlet. However, both the proximal end inlet and the distal end outlet are adjacent to the angled port.

The angled port has a proximal end 40, a distal end 42 and an axis BB which intersects longitudinal axis AA of the tube. The angled port has a length L2 and L3, as shown in FIG. 1. Length L2 can be greater than length L3. Length L2 can be from about 10 to about 30 mm. Length L2 can be about 10, 11, 12, 13, 14, 15, 16, 17, 18, 19, 20, 21, 22, 23, 24, 25, 26, 27, 28, 29 or 30 mm. Length L3 can be from about 5 to about 20 mm. Length L3 can be about 5, 6, 7, 8, 9, 10, 11, 12, 13, 14, 15, 16, 17, 18, 19 or 20 mm.

The proximal end of the angled port includes opening 44 which has a diameter D3, as shown in FIG. 1. Diameter D3 is less than or smaller than the diameter of D1 and/or D2. Diameter D3 can be from about 4 to about 10 mm. Diameter D3 can be about 4, 5, 6, 7, 8, 9 or 10 mm. It will be understood that the diameter of the angled port can also be the same diameter as the diameter of the tube or a diameter larger than the diameter of the tube.

Figure 3:
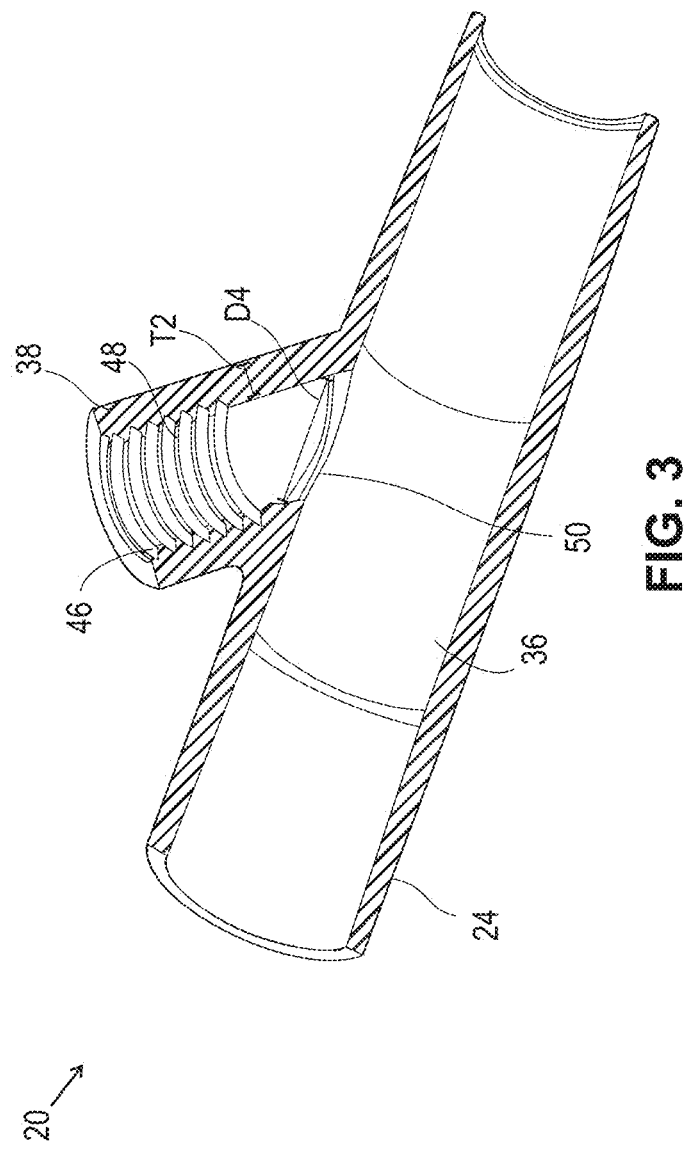
FIG. 3 illustrates a cross sectional view of the capnography fitting of FIG. 1.

The opening of the angled port leads into an inner surface 46 that comprises threading 48, as shown in FIG. 3. In some embodiments, the entire inner surface of the angled port is threaded or is at least partially threaded for engagement with a luer fitting, as described herein.

The distal end of the angled port intersects with the tube and allows gas flow in and/or out of the port. In some embodiments, the entire inner surface of the angled port is threaded or is at least partially threaded. The distal end of the port includes an opening 50 which has a diameter D4, as shown in FIG. 3. Like the port, the opening of the angled port is also angled. The opening is an opening in the inner surface of the tube that allows the angled port to intersect with the inner surface of the tube. In this way, the angled port and the tube are fluidly coupled and allow passage of gas into and out of the angled port and the tube.

The angled port is ideal for inserting a sampling tube into the tube and sampling gas, particularly gas exhaled by the patient and captured by the inhalation mask in order to obtain a capnography reading and monitor a patient's breathing pattern during the dental and/or medical procedure. Alternatively, the angled port can be ideal for sampling gas, particularly gas exhaled by the patient and captured by the inhalation mask from the port, without the need for a sampling tube, so that a capnography reading can be obtained directly from the angled port without the need to insert a sampling tube.

The bold arrow CC in FIG. 2 illustrates the typical direction of gas flow into the tube. The angled port provides easy access to connect to a capnography device and provides an ideal area to sample carbon dioxide exhaled from the patient during respiration.

The angled port is disposed at an acute angle relative to the exterior surface of the proximal end inlet of the tube and has an angle $\alpha1$, as shown in FIG. 2 of from about 10 to about 60 degrees or from about 10 to about 89 degrees relative to the exterior surface of the tube adjacent the proximal end inlet. In some embodiments, the angle $\alpha1$ is from about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 or 89 degrees relative to the exterior surface of the tube. The angled port is configured to allow at least a portion of a sampling tube, as described herein, to be slidably received by the inner surface of the angled port, into the inner surface of the tube to extend from the distal end outlet of the tube and into an inlet of the inhalation mask (e.g., nasal mask). In some embodiments, the angled port is configured to connect to a capnography machine at the proximal end, as described herein.

By the port being angled, the user can slide a sampling tube into the port from the port opening. The sampling tube will be guided to the interior of the tube and the sampling tube can extend out of the distal end of the tube and be positioned in the inlet of the nasal mask and extend into the interior of the nasal mask and adjacent to the nostril of the patient, when the nasal mask is worn. In this way, the sampling tube, which is movable and not fixedly attached to the interior of the mask, will be adjacent to the nostril and the user can obtain a capnography reading from exhaled gas in real time.

In some embodiments, the angled port is spaced a greater distance d2 from the distal end outlet than a distance d1 from the proximal end inlet. In some embodiments, the angled port is spaced at an equal distance from the proximal end inlet to the distal end outlet.

As shown in FIG. 3, the angled port has a thickness T2 that is greater than the thickness T1 of the tube. In some embodiments, thickness T2 may be less than or equal to T1. The thickness T2 can be from about 0.2 mm to about 4 mm. The thickness can be about 0.2, 0.3, 0.4, 0.5, 0.6, 0.7, 0.8, 0.9, 1, 2, 3 or 4 mm.

In some embodiments, the entire fitting can be a single monolithic unit. Molding techniques can create a monolithic fitting. Alternatively, the fitting is not a single monolithic unit and the components are molded separately. Molding techniques include, but are not limited to blow molding, over-molding, injection molding, casting, machining, stamping, or any other suitable manufacturing process. Further, when the fitting is not monolithic, components of the fitting, as described herein, can alternatively be attached by any attachment means, such as, for example, via adhesive, glue, molding, over molding, curing with UV light, welding, ultrasonically welding, mechanical attachment, or the like or combinations thereof.

In some embodiments, the capnography fitting can be rigid or semi-rigid. In some embodiments, the capnography fitting can be flexible and have a modulus of elasticity of about $1\times10^2$ to about $6\times10^5$ dynes/cm$^2$, or $2\times10^4$ to about $5\times10^5$ dynes/cm$^2$, or $5\times10^4$ to about $5\times10^5$ dynes/cm$^2$ or about $1\times10^2$ to about $6\times10^5$ dynes/cm$^2$, or $2\times10^4$ to about $5\times10^5$ dynes/cm$^2$, or $5\times10^4$ to about $5\times10^5$ dynes/cm$^2$.

Capnography System

Figure 4:
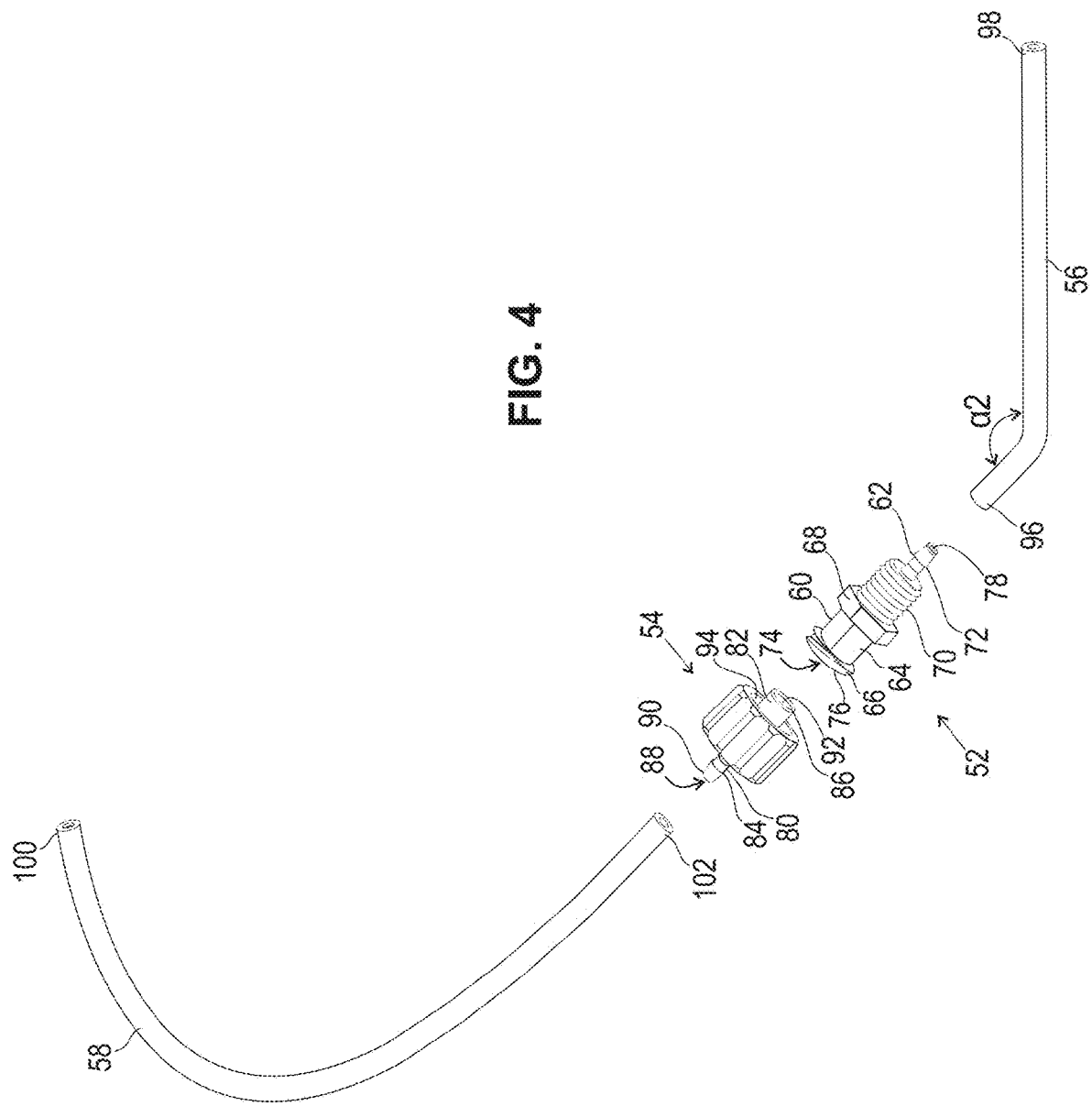
FIG. 4 illustrates an exploded view of a return conduit, a sampling tube, an internally threaded cap, and a luer fitting for use with the angled port of the capnography fitting of FIG. 1.
Figure 5:
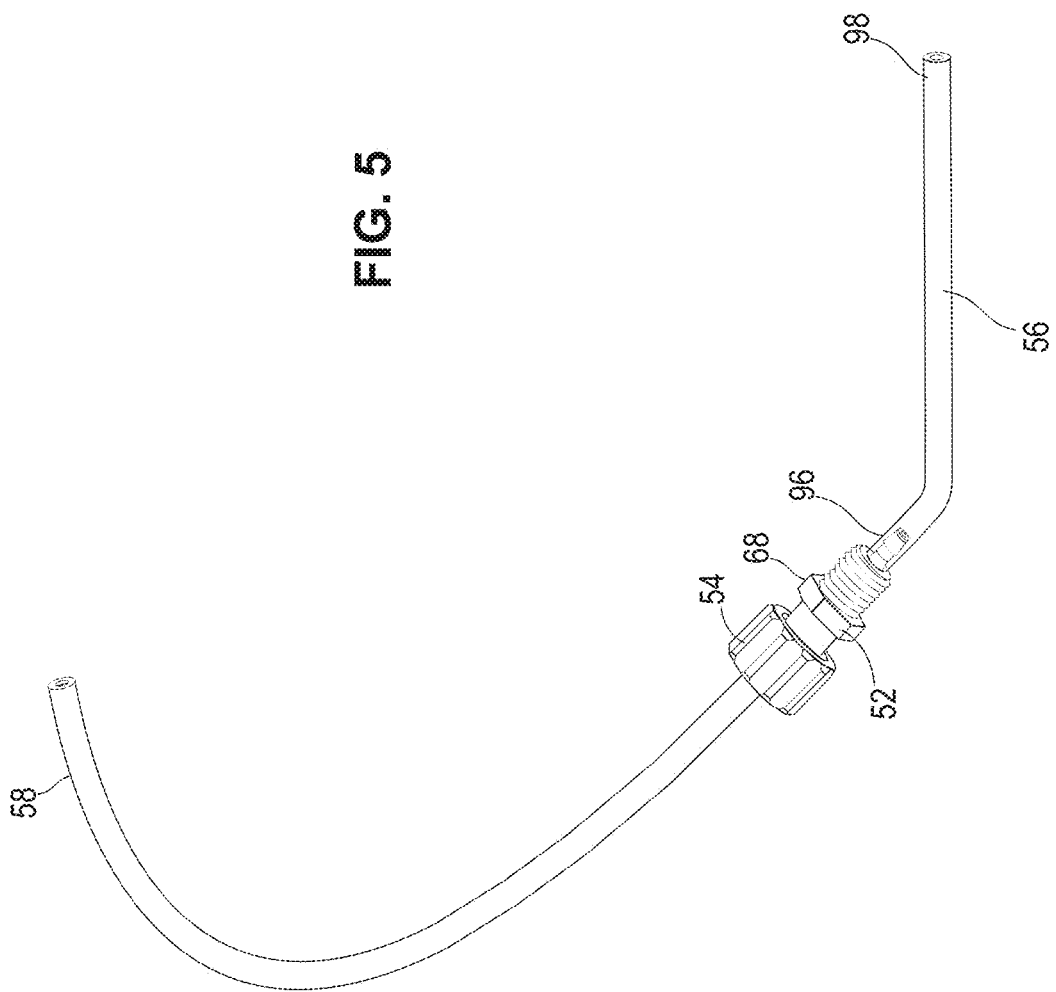
FIG. 5 illustrates a perspective view of the return conduit, sampling tube, internally threaded cap, and luer fitting of FIG. 4 in engagement.
Figure 6:
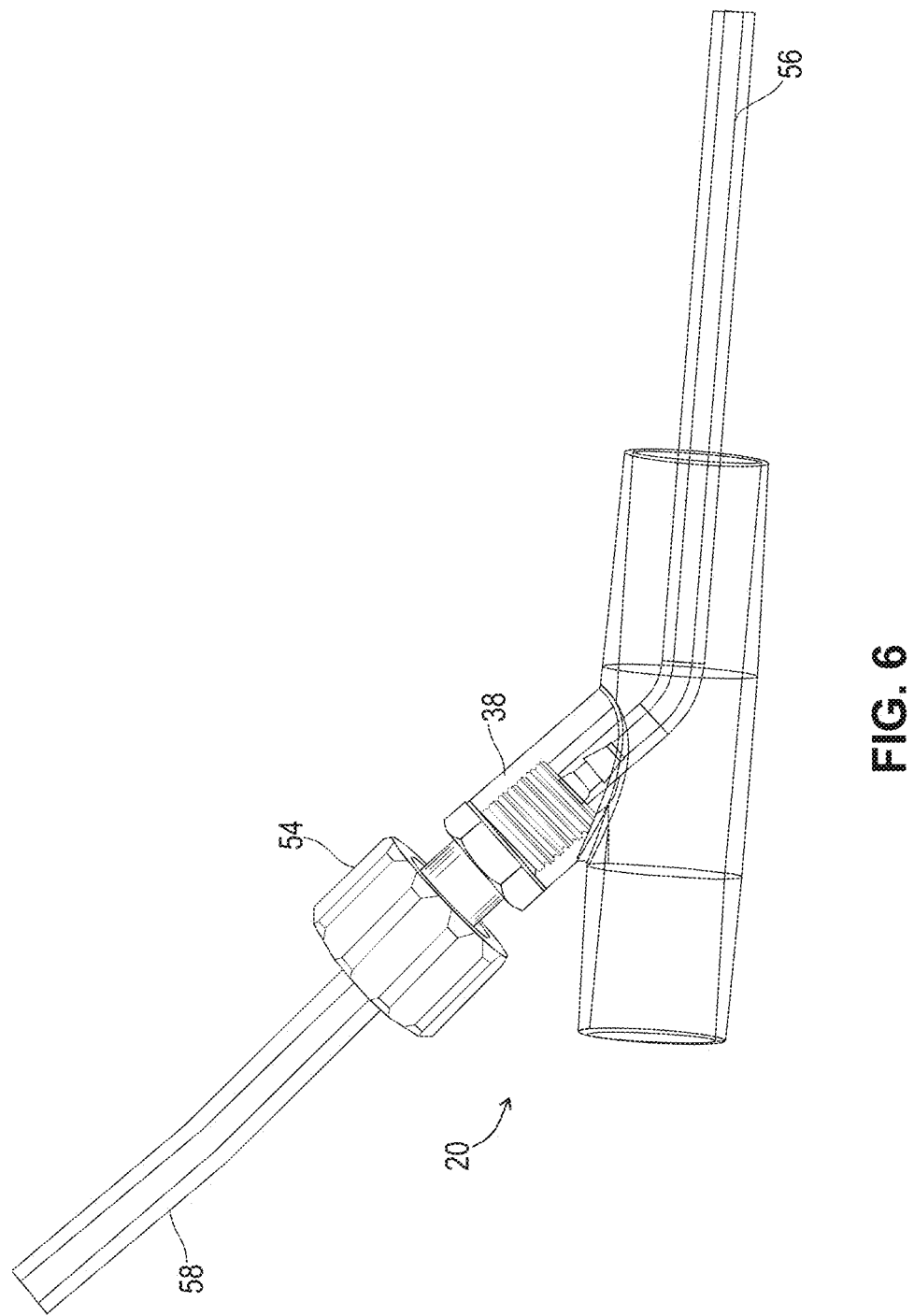
FIG. 6 illustrates a perspective view of the return conduit, sampling tube, internally threaded cap, and luer fitting of FIG. 4 engaged with the angled port of the capnography fitting of FIG. 1.

The angled port of the capnography fitting as described above, is configured to couple with a luer fitting, such as a female luer lock 52, an internally threaded cap 54, a sampling tube 56 and a return conduit 58, as shown in FIGS. 4-6. The luer fitting includes a proximal end 60 and a distal end 62. An exterior surface 64 defines a threaded portion 66 at the proximal end of the luer fitting. The threaded portion is configured to threadingly engage with an internally threaded portion of the internally threaded cap, as described below. The exterior surface 64 defines a flange 68, and at the distal end of the luer fitting, the exterior surface defines a threaded section 70 and a tapered section 72. The threaded section is configured for engagement with the threading on the inner surface of the angled port and the flange is configured for engagement with the proximal end of the port such that the luer fitting does not translate further into the angled port. A channel 74 having a first opening 76 and a second opening 78 is disposed longitudinally and through the center of the luer fitting.

The internally threaded cap extends between a first end 80 and a second end 82. The first end includes a first tip 84 and the second end includes a second tip 86. A channel 88 having openings 90 and 92 is disposed longitudinally and through the center of the cap. An internally threaded surface 94 is configured to engage with the threaded portion of the luer fitting and the second tip is configured for disposal in the first opening of the luer fitting such that the internally threaded cap and the luer fitting couple and/or lock together, as shown in FIG. 5.

The sampling tube can be flexible and extends between a first end 96 and a second end 98. The first end of the sampling tube engages with the tapered section of the luer fitting. The sampling tube is configured to engage the angled port such that at least a portion of the sampling tube is slidably received by the inner surface of the angled port, into the inner surface of the first tube to extend from the distal end outlet of the first tube and into an inlet of the inhalation mask. As shown in FIG. 4, the first end of the sampling tube can have an angle α2 that can be from about 5 to about 60 degrees, after it is slid into the fitting. In some embodiments, the angle α2 can be from about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 degrees.

The return conduit is flexible and extends between a first end 100 and a second end 102. The first end of the return conduit is configured to engage a portion of a capnography monitor and the second end of the return conduit is configured to engage the first tip of the internally threaded cap.

The sampling tube, as described herein, is configured to be slidably received by the inner surface of the angled port and can extend into the inner surface of the tube and extend from the distal end outlet of the tube and into an inlet of the inhalation mask (e.g., nasal mask). In some embodiments, the angled port is configured to connect to a capnography machine at the proximal end, as described herein.

By the port being angled, the user can slide a sampling tube into the port from the port opening. The sampling tube will be guided to the interior of the tube and the sampling tube can extend out of the distal end of the tube and be positioned in the inlet of the nasal mask and extend into the interior of the nasal mask and adjacent to the nostril of the patient, when the nasal mask is worn. In this way, the sampling tube, which is movable and not fixedly attached to the interior of the mask, will be adjacent to the nostril and the user can obtain a capnography reading from exhaled gas in real time.

In some embodiments, a capnography reading can be obtained without using the sampling tube. For example, the return conduit can be attached to a capnography monitor and the first tip of the internally threaded cap, as described above. The internally threaded cap engages the luer fitting which engages with the angled port. In this embodiment, the sampling tube is not attached to the luer fitting. In this embodiment, the angled port can be ideal for sampling gas, particularly gas exhaled by the patient and captured by the inhalation mask from the port, without the need for a sampling tube, so that a capnography reading can be obtained directly from the angled port without the need to insert a sampling tube.

In some embodiments, the length of the sampling tube and/or the return conduit can be cut into a desired length. The sampling tube can be cut into a desired length so as to access different areas of the mask in order to optimize a capnography reading such as a carbon dioxide reading. For example, an optimal reading can be obtained when the sampling tube has a longer length and the second end of the sampling tube is close to fresh gas.

In some embodiments, the sampling tube can alternatively engage the angled port via an interference fitting, press fitting or friction fitting. In this manner, the sampling tube is not attached to the luer fitting. Instead, the sampling tube has a slightly larger diameter or the same diameter as the angled port and is configured to be pressed or wedged into the opening at the proximal end of the angled port to provide a snug fit and the sampling tube is held in position by the angled port opening at the proximal end. In this embodiment, the sampling tube is still able to receive exhaled gas. In some embodiments, the sampling tube can also engage the angled port via a pressure fit, locking protrusion/recess, locking keyway and/or adhesive.

Figure 8:
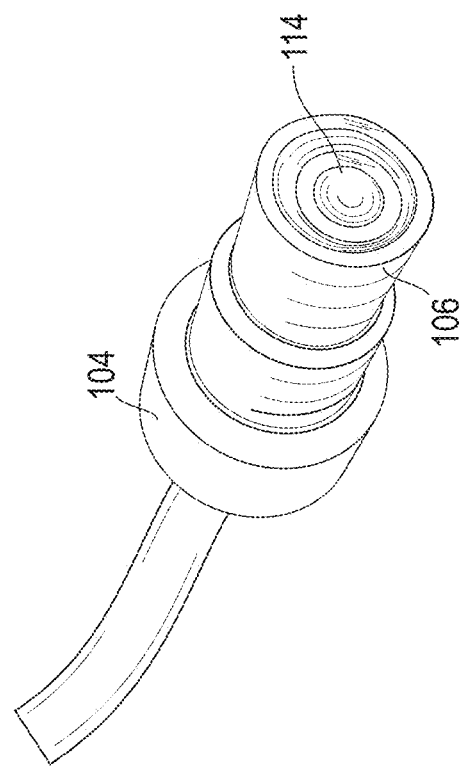
FIG. 8 illustrates a perspective view of the mixed gas fitting of FIG. 7.
Figure 7:
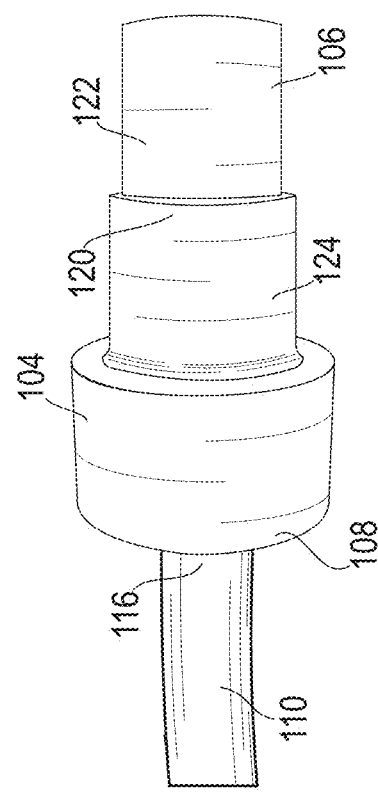
FIG. 7 illustrates a side view of a mixed gas fitting that couples to the capnography fitting of FIG. 1.
Figure 9:
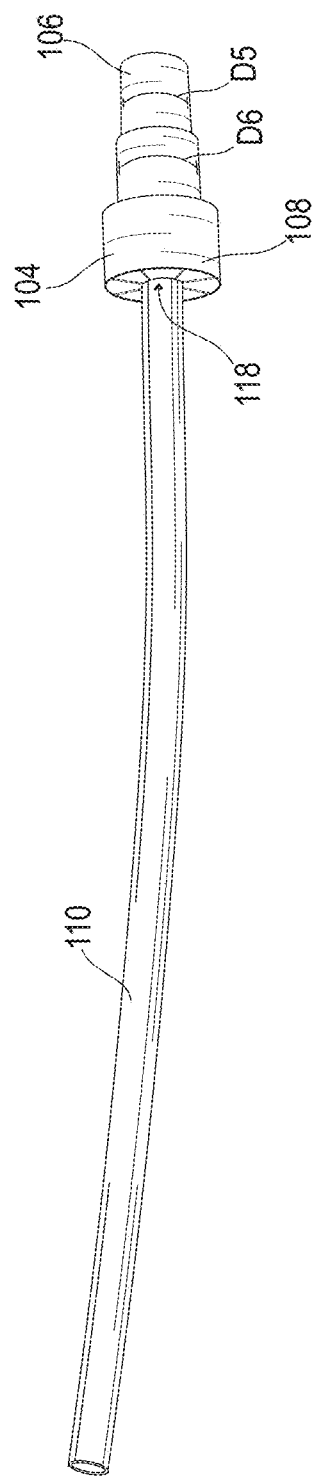
FIG. 9 illustrates a side view of the mixed gas fitting of FIG. 7.
Figure 10:
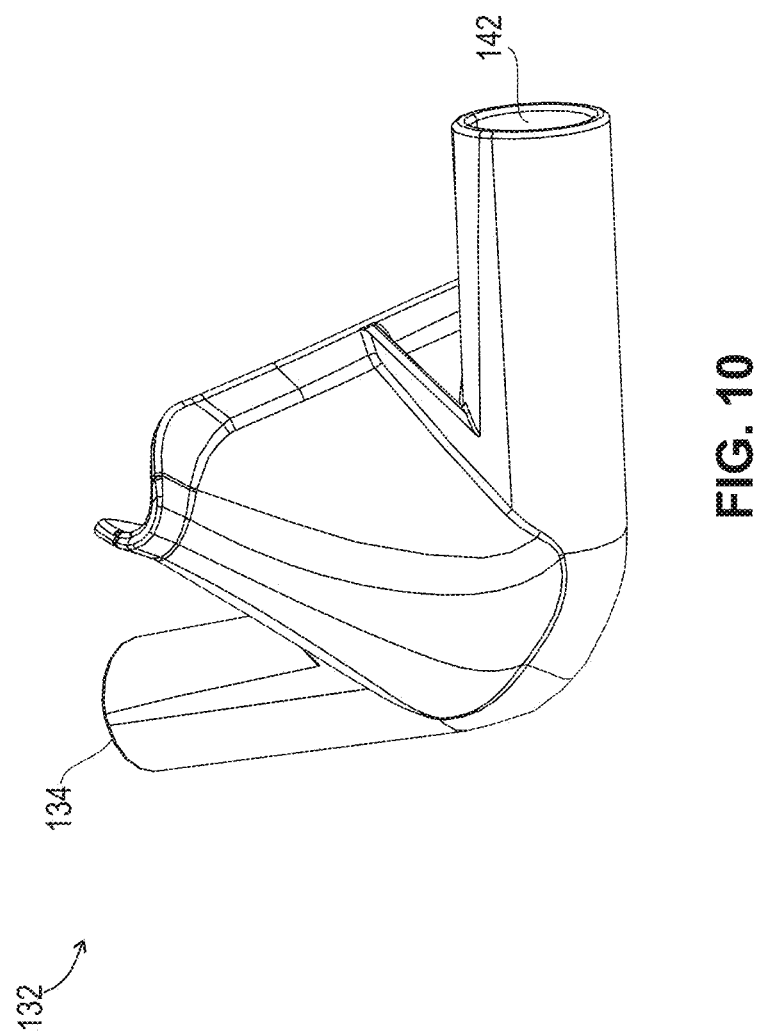
FIG. 10 illustrates a perspective front view of a nasal mask that is configured for engagement with the capnography fitting of FIG. 1.
Figure 12:
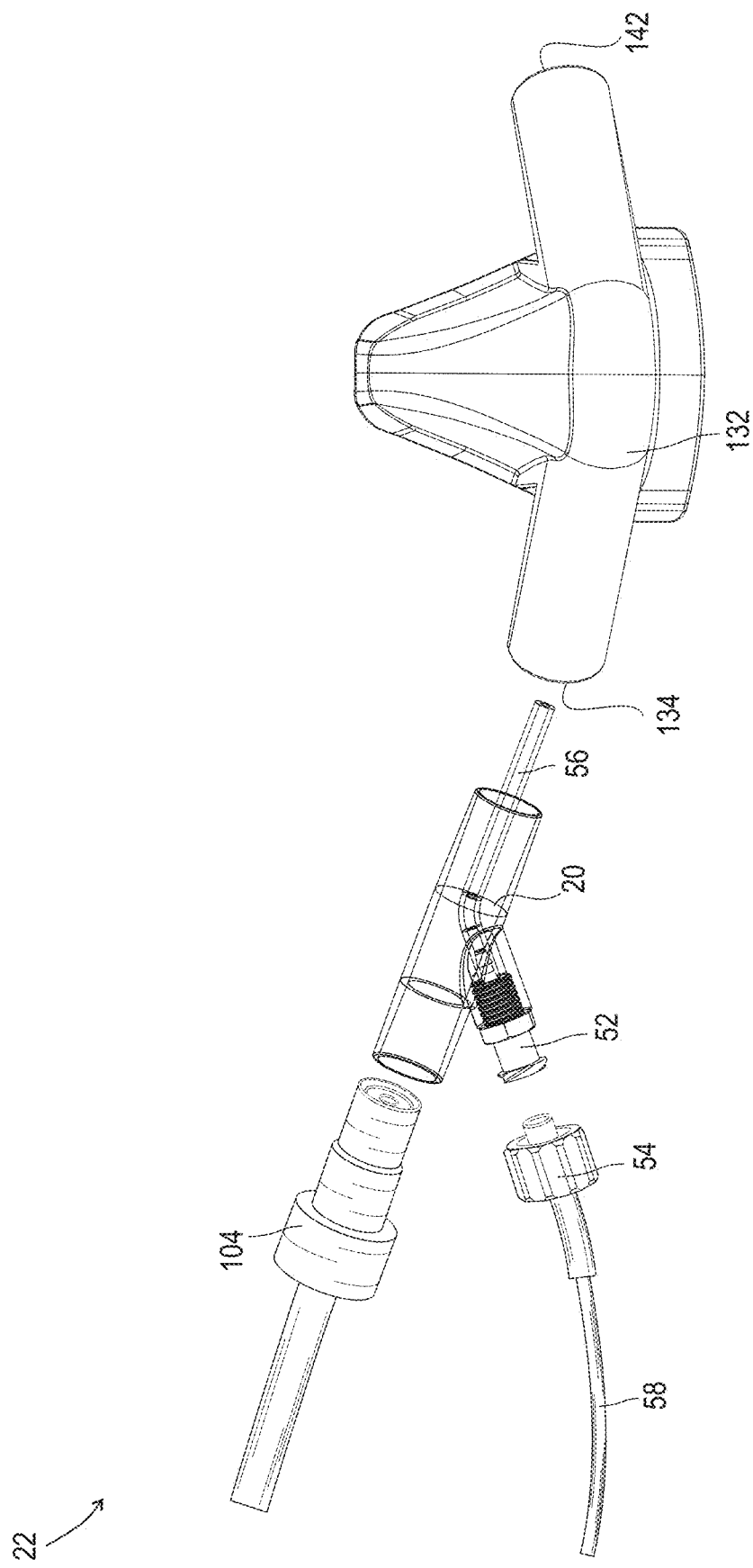
FIG. 12 illustrates a perspective view of components of a capnography system including the capnography fitting of FIG. 1, the mixed gas fitting of FIG. 7, and the return conduit, sampling tube, internally threaded cap, and luer fitting of FIG. 4.
Figure 13:
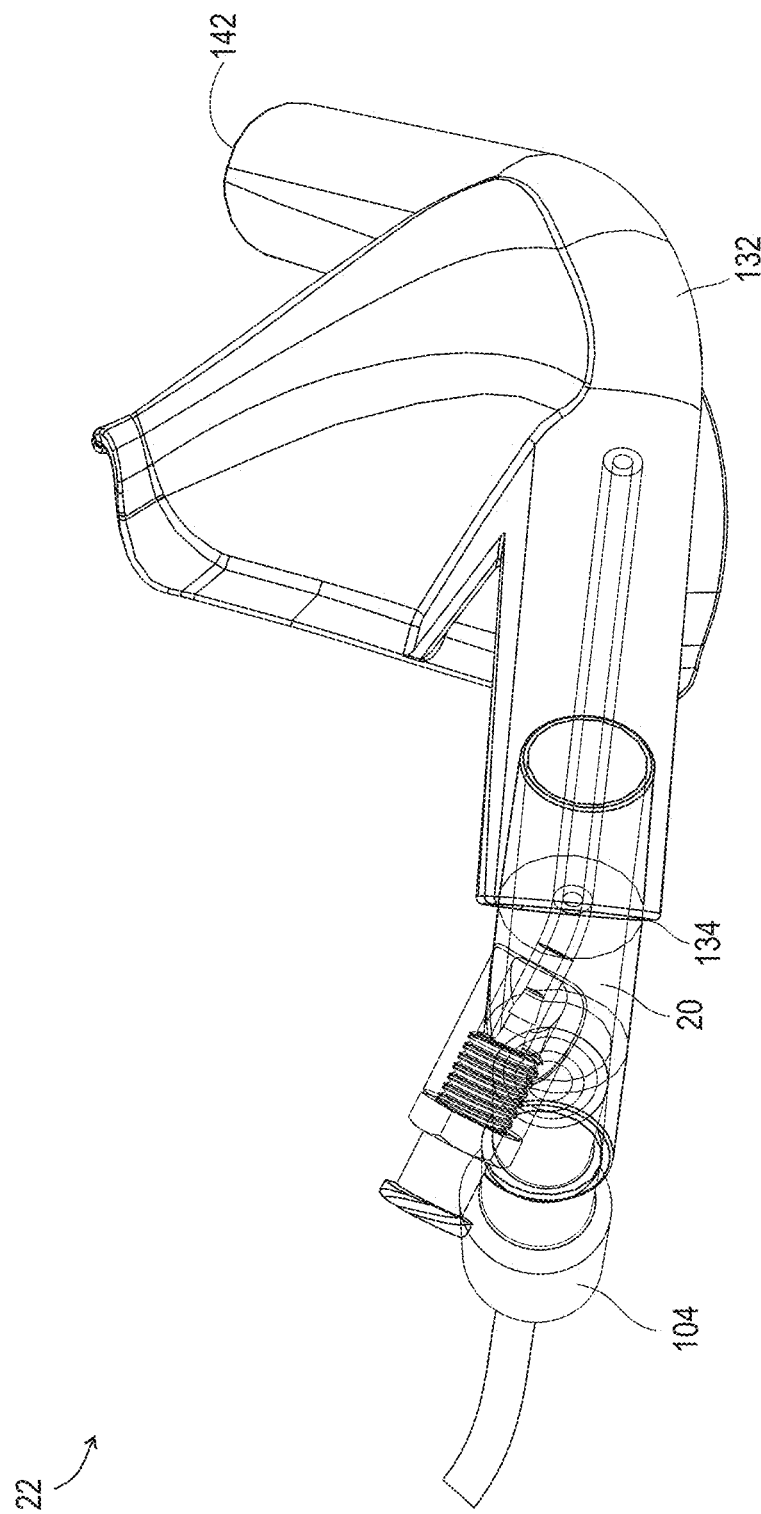
FIG. 13 illustrates a perspective view of the components of the capnography system of FIG. 12.
Figure 14:
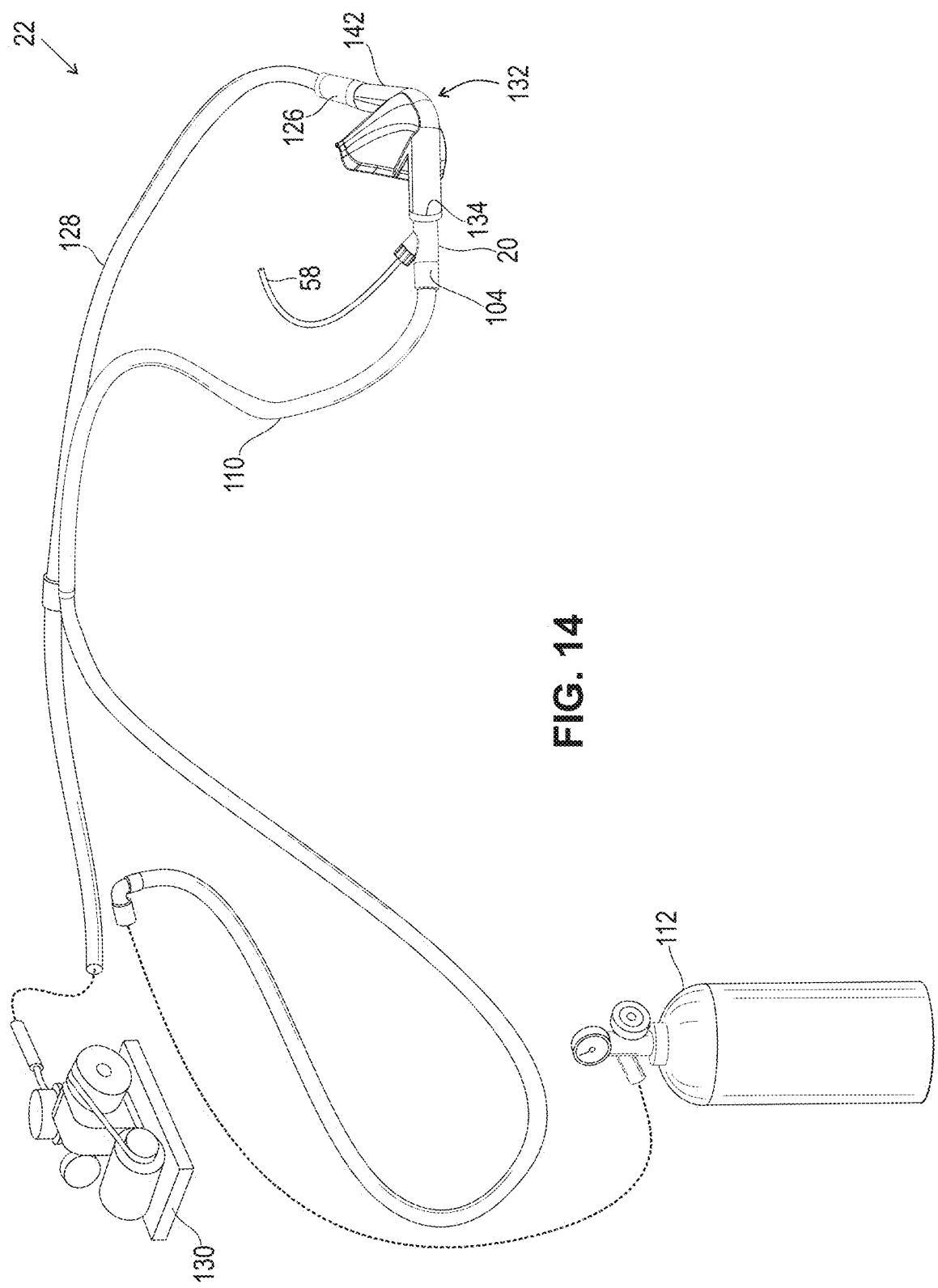
FIG. 14 illustrates a perspective view of the capnography system of FIG. 12 and further includes a delivery hose, a gas source, a vacuum hose, and a vacuum source.

The capnography system includes a mixed gas fitting 104, as shown in FIGS. 7-9. The proximal end inlet of the tube of the fitting is configured to engage with a first end 106 of the mixed gas fitting, as shown in FIG. 12-14. A second end 108 of the mixed gas fitting is configured to engage with a gas delivery hose 110 that attaches to a gas source 112 (FIG. 14) to provide gas, such as inhalation gas to the nasal mask. The gas delivery hose can be flexible and can have a modulus of elasticity that is less than the modulus of elasticity of the capnography fitting.

The mixed gas fitting includes an interior surface that defines a channel 114. The channel is configured for engagement with an end 116 of the gas delivery hose that is inserted into an opening 118 located at the second end of the mixed gas fitting.

The mixed gas fitting includes an exterior surface 120 that defines a first portion 122 and a second portion 124. The first portion is configured for slidable engagement with the proximal end inlet of the tube of the fitting. The first portion has a diameter D5 and the second portion has a diameter D6, as shown in FIG. 9. Diameter D5 is smaller than diameter D6 such that the proximal end inlet of the tube of the fitting only engages with the first portion and further translation of the fitting is prevented by the second portion. Diameter D5 is also smaller than diameter D1 of the proximal end inlet such that the first portion can slidably engage within the proximal end inlet. Diameter D5 can have a diameter of from about 3 to about 14 mm. Diameter D5 can have a diameter of about 3, 4, 5, 6, 7, 8, 9, 10, 11, 12, 13 or 14 mm. Diameter D6 can be the same or larger than diameter D1. Diameter D6 can have a diameter of from about 5 to about 18 mm. Diameter D6 can have a diameter of about 5, 6, 7, 8, 9, 10, 11, 12, 13, 14, 15, 16, 17 or 18 mm.

Figure 15:
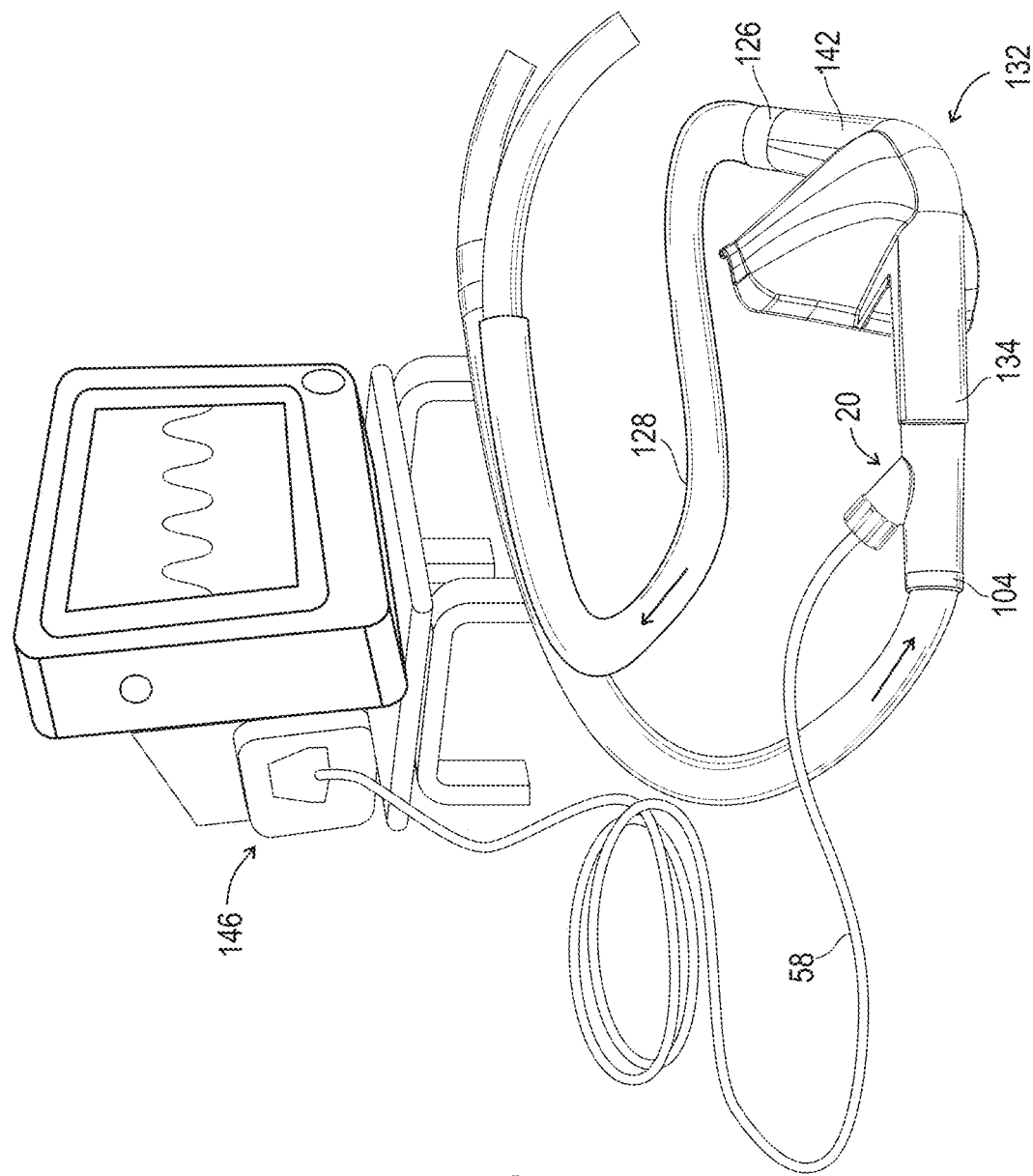
FIG. 15 illustrates a perspective view of the capnography system of FIG. 12 attached to a capnography monitor.

As shown in FIGS. 14 and 15, the capnography system includes a connector 126. The connector is similar to the connector assembly found and described in U.S. Patent Publication No. 2017/0361057, assigned to Accutron, Inc., which is incorporated herein by reference. A first end of the connector is configured to slidably engage with an outlet of the nasal mask, as described herein, and a second end is configured to engage a vacuum hose 128 that is connected to a vacuum source 130 to complete the capnography system circuit. Further, the connector is provided for conducting exhalation or exhaust gas from the mask. A suitable system operative for supplying a respirable gas to the mask and for providing a vacuum scavenger apparatus for collecting exhaust from the mask is fully disclosed in U.S. Pat. No. 5,311,862, of which is assigned to Accutron, Inc. and incorporated herein by reference.

As shown in FIGS. 10-15, a mask 132, such as a nasal mask is provided. The nasal mask is configured to administer respirable gas to a patient. Further, at least a portion of the sampling tube is configured to extend into the nasal mask, as described herein, such that a capnography reading can be taken close to the patient's nose for an accurate capnography reading. A nasal mask is available from Accutron, Inc. of Phoenix, Ariz. in scented and unscented flavors and adult, large adult and pediatric sizes under the name Axess™. Suitable nasal masks for use with the capnography fitting are described in U.S. Patent Publication No. 2017/0259018 assigned to Accutron, Inc. of Phoenix, Ariz.

Figure 11:
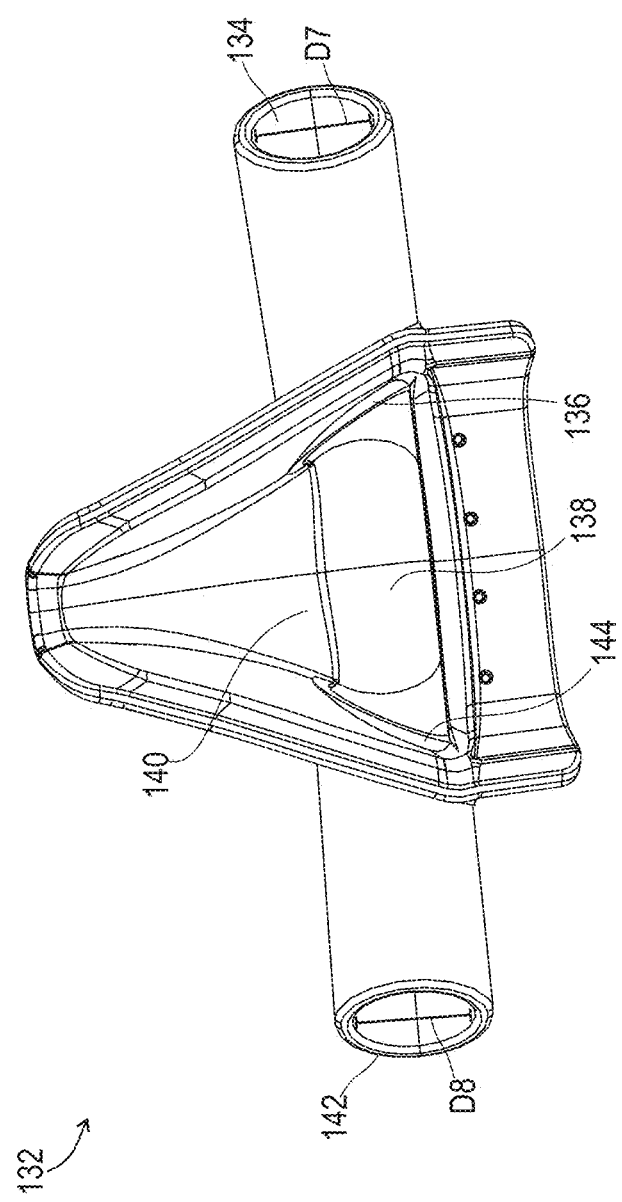
FIG. 11 illustrates a perspective back view of the nasal mask of FIG. 10.

The nasal mask includes an inlet 134 that is configured for engagement with the distal end outlet of the tube of the fitting, as shown in FIGS. 10-15. The inlet has a diameter D7, as shown in FIG. 11 that is larger than the diameter D2 of the distal end of the tube of the fitting. Diameter D7 can have a diameter of from about 6 to about 20 mm. Diameter D7 can have a diameter of about 6, 7, 8, 9, 10, 11, 12, 13, 14, 15, 16, 17, 18, 19 or 20 mm. An opening or outlet 136 is found on an interior surface 138 of the nasal mask and corresponds to the inlet. The sampling tube is slidably received by the inner surface of the angled port and into the inner surface of the tube. The sampling tube then extends from the distal end outlet of the tube and into the inlet of the nasal mask. From there, a portion of the sampling tube, such as the distal end of the sampling tube extends out of the outlet 136 and into a nasal chamber 140 of the nasal mask, as shown in FIGS. 11 and 12. Diameters D7 and D8 can be the same diameters or different diameters relative to each other.

The nasal mask includes an outlet 142 that is configured for engagement with the connector and/or the vacuum hose, as shown in FIGS. 14 and 15. The outlet has a diameter D8 that is larger than a diameter of an end of the connector and/or the vacuum hose. Diameter D8 can have a diameter of from about 4 to about 16 mm. Diameter D8 can have a diameter of about 4, 5, 6, 7, 8, 9, 10, 11, 12, 13 or 14 mm. An opening or inlet 144 is found on the interior surface 138 of the nasal mask and corresponds to the outlet. In some embodiments, the nasal mask is disposable and is not reusable which prevents cross contamination between users. The mask can also be various colors, sizes and scents. The nasal mask can also be unscented and can be translucent.

The nasal mask is a low-profile design that provides unencumbered access to the oral cavity of a patient. The nasal mask can be small and lightweight and allows a user to efficiently work on a patient. The nasal mask provides a comfortable fit and fits snugly on a user's face without the need for tape or uncomfortable tubes protruding into the patient's nostril. The nasal mask and the capnography system is lightweight, autoclavable, and minimizes drag and pull, which enhances patient comfort. In some embodiments, the nasal mask and the capnography system can minimize a user's exposure to ambient nitrous oxide gas.

Referring to FIGS. 12-14, the capnography fitting 20 is placed on the right side of the nasal mask 132 and is ideal for right-handed users, such as clinicians to install the capnography fitting 20 into the inlet of the mask. For left handed users, the capnography fitting 20 can be inserted in place of connector 126 on the left-hand side of the mask and the capnography fitting 20 can be switched with connector 126 on the right side of the mask as shown in FIG. 14. Thus, the capnography fitting 20 and connector 126 can easily be switched to the right side or left side of the mask based on the comfort of the user. Likewise, sampling of gas can be performed on the right or left side of the mask based on the comfort of the user.

Referring to FIG. 15, a capnography monitor 146 is provided. The capnography monitor is configured for engagement with the first end of the return conduit. In some embodiments, as described above, a portion of the capnography monitor can engage the first tip of the internally threaded cap directly without the use of the return conduit. The bold arrows in FIG. 15 illustrate typical directions of gas flow in the circuit.

Capnography Fitting Materials

The capnography fitting and/or components of the capnography system can be made from various materials. In some embodiments, the fitting and/or the components of the capnography system comprise a plastic material and can be a thermoplastic material. Suitable materials include, but are not limited to, polyurethane, polyurea, polyether(amide), PEBA, thermoplastic elastomeric olefin, copolyester, styrenic thermoplastic elastomer, carbon fiber, glass fiber, ceramics, methacrylates, poly (N-isopropylacrylamide), PEO-PPO-PEO (pluronics), rubber, plastic (e.g., polycarbonates), ABS, MABS, silicone, or the like or combinations thereof. In some embodiments, the components of the system can be made from a thermoplastic elastomer found under the trademark KRATON®. In some embodiments, the capnography fitting and its components can be clear plastic.

In some embodiments, the capnography system can use various lubricants in order to assist in engagement of components of the system. In some embodiments, the lubricant comprises an oil lubricant. The oil lubricant can be polydimethyl siloxane, polytrifluoropropylmethyl siloxane, or a copolymer of dimethylsiloxane and trifluoropropylmethylsiloxane. In other embodiments, non-silicone based lubricants can be used that include, without limitation, a water soluble lubricant, an insoluble lubricant, a viscous gel lubricant, a solid lubricant or a combination thereof. Water soluble lubricants include, without limitation, polyethylene oxide, polyvinylpyrrolidone, polyvinyl alcohol, and derivatives thereof.

In various embodiments, non-silicone lubricants can be used, include hydrophilic polymer coatings, Teflon (PTFE) lubricants and coatings, thermoplastic coatings, cyanoacrylate coatings, Parylene coatings, plasma surface treatments, cornstarch powder coatings liquid soaps, Astroglide lubricants, mineral oil, glycerin, alcohol, saline, Krytox lubricants, molybdenum disulfide lubricants and graphite.

Methods of Assembling and Use

A method of assembling a capnography system is provided, the method comprising providing a capnography fitting, the capnography fitting comprising a tube having a proximal end inlet and a distal end outlet, the tube having an angled port in fluid communication with and disposed adjacent to the proximal end inlet and the distal end outlet; inserting a first end of a mixed gas fitting into the proximal end inlet of the tube; coupling a second end of the mixed gas delivery fitting to a delivery hose that is attached to a vacuum source; coupling the distal end outlet of the tube to an inlet of a nasal mask; and coupling a connector to an outlet of the nasal mask that is engaged with a vacuum hose, the vacuum hose being connected to a vacuum source to assemble the capnography system.

In some embodiments, an inner surface of the angled port is configured to slidably receive at least a portion of a sampling tube, the sampling tube configured to extend out from the distal end outlet of the tube into the inlet and a nasal chamber of the nasal mask. In some embodiments, the angled port is configured to couple with a luer fitting and an internally threaded cap.

A method of monitoring a patient's respiratory functions is provided, the method comprising attaching a nasal mask to a nose of the patient, the nasal mask having an inlet to receive inhalation gas and an outlet to discharge exhalation gas, the nasal mask comprising a capnography fitting comprising a tube having a proximal end inlet and a distal end outlet, the tube having an angled port in fluid communication with and disposed adjacent to the proximal end inlet and the distal end outlet, the distal end outlet of the tube slidably engaging the inlet of the nasal mask; providing inhalation gas to the patient through the inlet of the nasal mask; and obtaining a sample of the exhalation gas from the angled port to monitor the patient's respiratory functions.

In some embodiments, an inner surface of the angled port is configured to slidably receive at least a portion of a sampling tube, the sampling tube configured to extend out from the distal end outlet of the tube into the inlet of the nasal mask. In some embodiments, at least a portion of the sampling tube extends into a nasal chamber of the nasal mask. In some embodiments, the patient's respiratory functions are patient breathing patterns and carbon dioxide levels produced from exhalations of the patient.

Kits

A kit is provided for capnography monitoring, the kit comprising a capnography fitting comprising a tube having a proximal end inlet and a distal end outlet, the tube having an angled port in fluid communication with and disposed adjacent to the proximal end inlet and the distal end outlet; and instructions for assembling the kit for capnography monitoring.

In some embodiments, the kit includes a mixed gas fitting comprising a first end configured to engage the proximal end inlet, and a second end configured to engage a gas delivery hose connected to a gas source; and a sampling tube configured to extend out of the distal end outlet of the tube.

In some embodiments, the kit includes a nasal mask having an inlet and an outlet, the inlet of the nasal mask configured to engage the distal end outlet of the tube, and the outlet of the nasal mask configured to engage a connector, the connector configured to engage a vacuum hose, and the vacuum hose configured to engage a vacuum source.

In various embodiments, the kit may include additional parts along with each component described in this disclosure, combined together to be used with the respective components. For example, the kit may include the capnography fitting in a first compartment. A second compartment may include the nasal mask. A third compartment may include the mixed gas fitting. A fourth compartment may include the connector. A fifth compartment may include the luer fitting, the internally threaded cap, the sampling tube and the return conduit. A sixth compartment may include the gas delivery hose and the vacuum hose. A seventh compartment may include a lubricant with or without gloves, drapes, wound dressings and other procedural supplies for maintaining sterility, as well as an instruction booklet. Each component of the kit (e.g., nasal mask, capnography fitting, connector, sampling tube, internally threaded cap, etc.) may be separately packaged in a plastic pouch that can be sterilized. A cover of the kit may include illustrations of the use of the device and a clear plastic cover may be placed over the compartments to maintain sterility.

The components of the kit for capnography monitoring may be lightweight, disposable and sterilizable. In various embodiments, one or more components of the kit can be sterilized by radiation in a terminal sterilization step in the final packaging. Terminal sterilization of a product provides greater assurance of sterility than from processes such as an aseptic process, which may require individual product components to be sterilized separately and the final package assembled in a sterile environment. Typically, in various embodiments, gamma radiation is used in the terminal sterilization step, which involves utilizing ionizing energy from gamma rays that penetrates into the components of the kit. Gamma rays are highly effective in killing microorganisms, they leave no residues nor have sufficient energy to impart radioactivity to the components of the kit. Gamma rays can be employed when the components of the kit are in the package and gamma sterilization does not require high pressures or vacuum conditions, thus, package seals and other components are not stressed. In addition, gamma radiation eliminates the need for permeable packaging materials.

In some embodiments, electron beam (e-beam) radiation may be used to sterilize one or more components of the kit. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize one or more components of the kit, including, but not limited to, gas sterilization, such as, for example, with ethylene oxide or steam sterilization.

Having now generally described the invention, the same may be more readily understood through the following reference to the following examples, which are provided by way of illustration and are not intended to limit the present invention unless specified.

EXAMPLES

Example 1: Port and Luer Lock Disposed in Tubing

The goal of this experiment was to provide a capnography fitting or connection in a low profile nasal hood (e.g., mask) system. The fitting or connection included a port having a female luer lock connection disposed on the outside of the tubing and near the mask. The purpose was to provide a suitable pathway to the mask where a reliable reading could be obtained. Alternatively, direct readings could be taken from the fitting alone and not from the luer lock.

A hole punch was used to create the hole in the tubing. The fitting was disposed in the hole and a small sampling tube was then passed into the fitting. A portion of the sampling tube was then inserted into the interior of the mask.

Results showed that a good capnography reading was obtained however, the port and luer lock of the fitting were hard to assemble and overall, the fitting was loose. Because of this, the fitting did not work well. Further, once the fitting was in the tube, it was impossible to add the sampling tube. Since the sampling tube could not be added after the fitting was disposed into the hole, researchers made a second attempt to attach the sampling tube to the fitting first. However, it was difficult to press the sampling into the tube properly. It was concluded that a different method or fitting was needed and it was suggested that a threaded luer lock might work correctly.

Example 2: Single Tubed Capnography Fitting

After the first fitting was made in Example 1, the current capnography fitting as described above regarding capnography fitting 20 was made. The fitting was placed in the capnography system and a flow was set at 7.0 IPM. The vacuum was set to green (45 IPM). Results showed that the current capnography fitting worked and that clear signals were generated by a capnography monitor.

Example 3: Double Tubed Capnography Fitting

After the first and second fittings of Examples 1 and 2 were made, a double tube capnography fitting was made compatible with a Clearview™ nasal mask. The fitting was placed in the capnography system and a flow was set at 7.0 IPM. The vacuum was set to green (45 IPM). Results showed that the current capnography fitting worked and that clear signals were generated by a capnography monitor.

The present invention has been described above with reference to a preferred embodiment. However, those skilled in the art will recognize that changes and modifications may be made in the described embodiments without departing from the nature and scope of the present invention. Various changes and modifications to the embodiment herein chosen for purposes of illustration will readily occur to those skilled in the art. To the extent that such modifications and variations do not depart from the spirit of the invention, they are intended to be included within the scope thereof.

What is claimed is:

1. A fitting comprising a rigid tube having a proximal end inlet having a first diameter and configured to receive an inhalation gas, and to slidably engage a mixed gas fitting comprising a first end, a second end, an interior surface defining a channel configured for engagement with a gas delivery hose at the second end, an exterior surface that defines a first portion on the first end and a second portion on the second end, the first portion having a second diameter and th second diameter is smaller than the first diameter and the second diameter is smaller than the third diameter, wherein the second diameter is smaller than the first diameter and the third diameter such that the proximal end inlet of the rigid tube engages only with the first portion at the first end and further translation of the fitting is prevented by the second portion, and the rigid tube having a distal end outlet configured to slidably engage directly to an inlet of an inhalation mask configured to cover a nose and/or mouth, the rigid tube having an angled port comprising an opening that leads to an inner surface that comprises threading, the angled port configured to couple with a luer fitting comprising a female luer lock, an internally threaded cap, a sampling tube and a return conduit configured to engage a portion of a capnography monitor via a first return conduit end and to engage the internally threaded cap via a second return conduit end, the angled port being in fluid communication with and disposed adjacent to the proximal end inlet or the distal end outlet; wherein the fitting is a capnography fitting for use in a capnography system and wherein the capnography fitting is configured to fit inhalation masks of various sizes and shapes so that viable carbon dioxide readings can be obtained from an air sample obtained from a patient's exhaled gas.

2. The fitting of claim 1, wherein the angled port has a diameter smaller than a diameter of the proximal end inlet and the distal end outlet of the rigid tube.

3. The fitting of claim 1, wherein the angled port is disposed at an acute angle relative to a surface of the proximal end inlet of the rigid tube.

4. The fitting of claim 1, wherein the inner surface of the angled port and an inner surface of the rigid tube are configured to receive athe sampling tube configured to connect to a capnography device.

5. The fitting of claim 4, wherein the sampling tube is flexible and extends out from the distal end outlet of rigid the tube.

6. The fitting of claim 1, wherein the inner surface of the angled port is configured to slidably receive at least a portion of the sampling tube, which is configured to extend from the distal end outlet into the inlet of the inhalation mask.

7. A capnography fitting comprising a rigid tube having a proximal end inlet having a proximal end diameter and is configured to receive an inhalation gas, and to slidably engage a mixed gas fitting, and a distal end outlet, the rigid tube having an angled port comprising an opening that leads to an inner surface that comprises threading, the angled port configured to couple with a luer fitting comprising a female luer lock, an internally threaded cap, a sampling tube and a return conduit configured to engage a portion of a capnography monitor via a first return conduit end and to engage the internally threaded cap via a second return conduit end, the angled port being in fluid communication with and disposed adjacent to the proximal end inlet and the distal end outlet, the angled port configured to slidably receive at least a portion of the sampling tube, the sampling tube being configured to extend from the distal end outlet of the rigid tube into a nasal chamber of a nasal mask, and the distal end outlet configured to slidably engage directly to an inlet of thea nasal mask; wherein the fitting is a capnography fitting for use in a capnography system and wherein the capnography fitting is configured to fit nasal masks of various sizes and shapes so that viable carbon dioxide readings can be obtained from an air sample obtained from a patient's exhaled gas; and wherein the mixed gas fitting comprises a first end, a second end, an interior surface defining a channel configured for engagement with a gas delivery hose at the second end, an exterior surface that defines a first portion on the first end and a second portion on the second end, the first portion having a first portion diameter and the second portion having a second portion diameter larger than the proximal end diameter, wherein the first portion diameter is smaller than the proximal end diameter and the first portion diameter is smaller than the second portion diameter such that the proximal end inlet of the rigid tube engages only with the first portion at the first end and further translation of the fitting is prevented by the second portion.

8. The fitting of claim 7, wherein the angled port has a diameter smaller than a diameter of the proximal end inlet and the distal end outlet of the rigid tube.

9. A kit for capnography monitoring, the kit comprising a capnography fitting comprising a rigid tube having a proximal end inlet having a first diameter and configured to receive an inhalation gas, and to slidably engage a mixed gas fitting comprising a first end, a second end, an interior surface defining a channel configured for engagement with a gas delivery hose at the second end, an exterior surface that defines a first portion on the first end and a second portion on the second end, the first portion having a second diameter and the second portion having a third diameter larger than the first diameter, wherein the second diameter is smaller than the first diameter and the second diameter is smaller than the third diameter such that the proximal end inlet of the rigid tube engages only with the first portion at the first end and further translation of the fitting is prevented by the second portion, and a distal end outlet configured to slidably engage directly to an inlet of an inhalation mask configured to cover a nose and/or mouth and comprising an inlet and an outlet, the inlet of the inhalation mask configured to directly engage the distal end outlet of the rigid tube, and the outlet of the inhalation mask configured to engage a connector, the connector configured to engage a vacuum hose, and the vacuum hose configured to engage a vacuum source, the rigid tube having an angled port comprising an opening that leads to an inner surface that comprises threading, the angled port configured to couple with a luer fitting comprising a female luer lock, an internally threaded cap, a sampling tube and a return conduit configured to engage a portion of a capnography monitor via a first return conduit end and to engage the internally threaded cap via a second return conduit end, the angled port being in fluid communication with and disposed adjacent to the proximal end inlet and the distal end outlet; and instructions for assembling the kit for capnography monitoring; wherein the capnography fitting is for use in a capnography system and wherein the capnography fitting is configured to fit inhalation masks of various sizes and shapes so that viable carbon dioxide readings can be obtained from an air sample obtained from a patient's exhaled gas.

10. The kit of claim 9, further comprising the mixed gas fitting.

11. The kit of claim 9, further comprising the inhalation mask.

\* \* \* \* \*

UNITED STATES PATENT AND TRADEMARK OFFICE
CERTIFICATE OF CORRECTION

PATENT NO. : 11,696,996 B2
APPLICATION NO. : 16/446743
DATED : July 11, 2023
INVENTOR(S) : VanPelt Page 1 of 1

It is certified that error appears in the above-identified patent and that said Letters Patent is hereby corrected as shown below:

In the Claims

At Column 15, Line 25, "th" should be -- the second portion having a third diameter larger than the first diameter, wherein the --.

At Column 15, Line 57, "athe" should be -- the --.

At Column 16, Line 17, "thea" should be -- the --.

Signed and Sealed this
Thirteenth Day of May, 2025

Coke Morgan Stewart
*Acting Director of the United States Patent and Trademark Office*